United States Patent
Bae et al.

(10) Patent No.: US 9,360,552 B2
(45) Date of Patent: Jun. 7, 2016

(54) APPARATUS AND METHOD FOR CREATING TISSUE DOPPLER IMAGE USING SYNTHETIC IMAGE

(75) Inventors: Moo Ho Bae, Seoul (KR); Jeong Ho Ham, Seoul (KR)

(73) Assignee: Samsung Medison Co., Ltd., Hongcheon-gun, Gangwon-do (KR)

(*) Notice: Subject to any disclaimer, the term of this patent is extended or adjusted under 35 U.S.C. 154(b) by 531 days.

(21) Appl. No.: 12/739,319

(22) PCT Filed: Oct. 24, 2008

(86) PCT No.: PCT/KR2008/006319
§ 371 (c)(1),
(2), (4) Date: Apr. 22, 2010

(87) PCT Pub. No.: WO2009/054706
PCT Pub. Date: Apr. 30, 2009

(65) Prior Publication Data
US 2010/0234729 A1 Sep. 16, 2010

(30) Foreign Application Priority Data

Oct. 25, 2007 (KR) .................. 10-2007-0107947
Sep. 29, 2008 (KR) .................. 10-2008-0095110

(51) Int. Cl.
*A61B 8/00* (2006.01)
*G01S 15/89* (2006.01)
(Continued)

(52) U.S. Cl.
CPC ........... *G01S 15/8979* (2013.01); *A61B 8/5276* (2013.01); *G01S 7/52026* (2013.01);
(Continued)

(58) Field of Classification Search
CPC ............. A61B 8/00; A61B 8/488; A61B 8/56
USPC .......................... 600/407, 437–449, 453–457
See application file for complete search history.

(56) References Cited

U.S. PATENT DOCUMENTS 4,972,838 A   11/1990  Yamazaki
5,438,994 A    8/1995  Starosta et al.
(Continued)

FOREIGN PATENT DOCUMENTS

EP   1 548 462 A1   6/2005
JP   2-126836        5/1990
(Continued)

OTHER PUBLICATIONS

European Search Report, issued in European Patent Application No. 08018527.5, dated Mar. 26, 2009.
(Continued)

*Primary Examiner* — Vani Gupta
(74) *Attorney, Agent, or Firm* — McDermott Will & Emery LLP

(57) ABSTRACT

An apparatus and method capable of producing a tissue Doppler image without repeatedly transmitting ultrasound signals by the ensemble number to each scan line. An ultrasound beam is transmitted in a non-sequential manner and a plurality of receive beams received in response to each transmission of the transmit beam are grouped into an increment data group of a scan line index increasing direction and a decrement data group of a scan line index decreasing direction. Auto correlation is performed on the increment data group of the scan line index ascending order and decrement data group of the scan line index descending order, weights are applied to respective auto correlation values for the increment and decrement data group, and then the auto correlation values with the weight applied are summed to compute a mean phase. At least one of velocities, powers and variances in response to the mean phase is outputted to produce TDI.

15 Claims, 3 Drawing Sheets

(51) Int. Cl.
*G01S 7/52* (2006.01)
*A61B 8/08* (2006.01)

(52) U.S. Cl.
CPC ......... *G01S 7/52028* (2013.01); *G01S 7/52046* (2013.01); *G01S 7/52085* (2013.01); *G01S 15/8997* (2013.01); *A61B 8/00* (2013.01); *A61B 8/08* (2013.01); *A61B 8/488* (2013.01); *A61B 8/52* (2013.01); *A61B 8/56* (2013.01); *G01S 7/52047* (2013.01); *G01S 7/52049* (2013.01); *G01S 7/52077* (2013.01); *G01S 7/52095* (2013.01)

(56) References Cited

U.S. PATENT DOCUMENTS

| | | | |
|---|---|---|---|
| 5,462,058 A * | 10/1995 | Yamada et al. | 600/454 |
| 5,738,098 A * | 4/1998 | Brock-Fisher et al. | 600/472 |
| 5,785,654 A | 7/1998 | Iinuma et al. | |
| 5,961,462 A | 10/1999 | Loupas et al. | |
| 6,126,604 A | 10/2000 | Bae et al. | |
| 6,186,950 B1 * | 2/2001 | Averkiou et al. | 600/443 |
| 6,193,662 B1 * | 2/2001 | Hwang | 600/447 |
| 6,283,918 B1 | 9/2001 | Kanda et al. | |
| 6,352,508 B1 | 3/2002 | Pang et al. | |
| 6,402,694 B1 | 6/2002 | Bae et al. | |
| 6,514,206 B2 * | 2/2003 | Maxwell et al. | 600/443 |
| 2004/0102702 A1 | 5/2004 | Shimazaki | |
| 2005/0203390 A1 | 9/2005 | Torp et al. | |
| 2008/0139938 A1 * | 6/2008 | Yang et al. | 600/445 |
| 2008/0239342 A1 * | 10/2008 | Lieberman | 358/1.9 |

FOREIGN PATENT DOCUMENTS

| | | |
|---|---|---|
| JP | 07-008492 A | 1/1995 |
| JP | 9-201361 | 8/1997 |
| JP | 10-127634 | 5/1998 |
| JP | 11-164833 | 6/1999 |
| JP | 11-342128 | 12/1999 |
| JP | 2006-223736 A | 8/2006 |
| JP | 2007-222674 A | 9/2007 |
| KR | 10-1999-0024624 | 4/1999 |
| KR | 10-2000-0073097 | 12/2000 |
| WO | WO 2007/049228 A1 | 5/2007 |

OTHER PUBLICATIONS

European Search Report, issued in European Patent Application No. 08018528.3, dated Mar. 30, 2009.
International Search Report issued in International Patent Application No. PCT/KR2008/006319, dated Jun. 9, 2009.
Niels Oddershede et al., "Motion compensated beamforming in synthetic aperture vector flow imaging", 2006 IEEE Ultrasonics Symposium, pp. 2027-2031, IEEE.
K.L. Gammelmark, et al., "Duplex Synthetic Aperture Imaging with Tissue Motion Compensation", 2003 IEEE Ultrasonics Symposium, pp. 1569-1573, IEEE.
B. Tavli et al., "Correlation Processing for Correction of Phase Distortions in Subaperture Imaging", IEEE Transactions on Ultrasonics Ferroelectrics and Frequency Control, Nov. 1, 1999, vol. 46 No. 6, pp. 1477-1488, IEEE.
C. Kasai et al., "Real-Time Two-Dimensional Blood Flow Imaging Using an Autocorrelation Technique", IEEE Transactions on Sonics and Ultrasonics, May 1985, vol. SU-32, No. 3, IEEE.
Moo-Ho Bae et al., "A New Motion Estimation and Compensation Method for Real-Time Ultrasonic Synthetic Aperture Imaging", IEEE Ultrasonic Symposium, 2007, pp. 1511-1513, IEEE.
B. Tavh et al., "An Efficient Motion Estimation Technique for ultrasonic Subaperture Imaging", Proceedings of the 20the Annual International Conference of the IEEE Engineering in Medicine and Biology Society, 1998, vol. 20 No. 2, pp. 816-819, IEEE.
Korean Office Action issued in Korean Patent Application No. 10-2008-0104674, dated Jun. 24, 2010.
Korean Office Action issued in Korean Patent Application No. 10-2008-0104676, dated Jun. 29, 2010.
Japanese Notice of Reason for Rejection, w/ English translation thereof, issued in Japanese Patent Application No. JP 2010-530936 dated Sep. 10, 2013.
European Search Report issued in application No. 08842438.7 issued on May 21, 2012.
Bilge et al., "Motion Estimation Using Common Spatial Frequencies in Synthetic Aperture Imaging", 1996 IEEE Ultrasonics Symposium, pp. 1551-1554.

* cited by examiner (2a)   (2b)   (2c)

APPARATUS AND METHOD FOR CREATING TISSUE DOPPLER IMAGE USING SYNTHETIC IMAGE

RELATED APPLICATIONS

This application is the U.S. National Phase under 35 U.S.C. §371 of International Application No. PCT/KR2008/006319, filed on Oct. 24, 2008, which in turn claims the benefit of Korean Application Nos. 10-2007-0107947, filed on Oct. 25, 2007, and 10-2008-0095110, filed on Sep. 29, 2008, the disclosures of which Applications are incorporated by reference herein.

TECHNICAL FIELD

The disclosure generally relates to an apparatus and a method for creating a tissue Doppler image, and more particularly to an apparatus and a method for forming a tissue Doppler image using a synthetic image.

BACKGROUND

An image processing system, which is used for processing and displaying an image of a target object, is implemented in various fields. The image processing system may include an image processing system for an ultrasound diagnosis (hereinafter referred to as "ultrasound diagnostic system").

The ultrasound diagnostic system transmits an ultrasound signal from the surface of a human body toward a desired portion within a target object. This allows an ultrasound image of soft tissues or blood flow to be obtained through non-invasive means by using information obtained through ultrasound echo signals. Compared to other medical imaging systems such as X-ray diagnostic systems, X-ray CT scanners, MRIs and nuclear medicine diagnostic systems, the ultrasound diagnostic system is advantageous since it is small in size and fairly inexpensive. Further, the ultrasound diagnostic system is capable of providing a real-time display and is highly safe without any dangerous side effects such as exposure to X-rays, etc. Thus, the ultrasound diagnostic system is extensively utilized for diagnosing the heart, abdomen and urinary organs, as well as widely applied in the fields of obstetrics, gynecology, etc.

Reflectivity of the ultrasound signals in blood flow is different from that in a myocardium. The reflectivity of the ultrasound signal in blood flow is relatively low while its moving velocity is more rapid than myocardial velocity. On the contrary, although myocardial velocity is relatively slow, the reflectivity of the ultrasound signal in the myocardium is very high. By using such a disparity of reflectivity in blood flow and the myocardium, a component of ultrasound signals reflected from the blood flow may be removed so that the myocardial velocity may be measured. A tissue Doppler image (TDI) indicating the measured myocardial velocity may be used to evaluate a myocardial function.

The TDI may transmit ultrasound signals to a target object along one scan line with an identical acoustic field at a constant time interval, receive reflected ultrasound signals from the target object, and detect a phase shift of received ultrasound signals to thereby compute a mean Doppler frequency by using auto correlation. This enables a color image of the target object to be displayed. The TDI may be applicable for assessing objective systolic and diastolic myocardial velocities, determining regional dysfunction and quantitatively assessing the myocardial velocities. The TDI may be helpful in following up cardiac functions from congenital and acquired cardiac diseases.

To configure TDI receiving scan lines according to the prior art, an ensemble number of transmit scan lines of the same position are required for calculation. Further, an auto correlation is performed upon received signals to form the TDI. That is, the ultrasound signal is repeatedly transmitted to one scan line by the ensemble number N (e.g., N ultrasound transmissions to a first scan line, N ultrasound transmissions to a second scan line, N ultrasound transmissions to a third scan line . . . ). Then, the received signals are synthesized to produce the TDI. For example, assuming that 10 scan lines are required for one TDI, the ultrasound signal should be repeatedly transmitted to each of the scan lines by the ensemble number N (10 N ultrasound transmissions) such that it requires a long time to produce the TDI. Especially, a frame rate is determined depending on a region of interest, an ensemble number, an interleaving number and the like. The conventional method of producing the TDI repeatedly transmits the ultrasound signal to each scan line by the ensemble number. This increases delay with increasing ensemble number. This delay causes a problem in that the frame rate decreases.

SUMMARY

It is an object of the present subject matter to provide an apparatus and method capable of creating a tissue Doppler image with a synthetic image at a high rate without repeatedly transmitting ultrasound signals by the ensemble number to each scan line.

An aspect of the disclosure encompasses an apparatus and a method capable of producing a tissue Doppler image without repeatedly transmitting ultrasound signals by the ensemble number to each scan line. An ultrasound beam is transmitted in a non-sequential manner. Also, a plurality of receive beams received in response to each transmission of the transmit beam are grouped into an increment data group of a scan line index increasing direction and a decrement data group of a scan line index decreasing direction. Auto correlation is performed for the increment and decrement data groups of the scan line increasing and decreasing directions. Thereafter, weights are applied to respective auto correlation values for the increment and decrement data group, and the auto correlation values with the weight applied are summed to compute a mean phase. At least one of velocities, powers, variances in response to the mean phase is outputted to produce TDI. In such a case, the non-sequential manner is achieved by setting a plurality of scan lines, defining sequential indices of the scan lines, setting an order of the transmit beam for the scan lines in a non-sequential manner in which increment and decrement of the indices are repeated, and transmitting the transmit beam according to the set transmit order. In order to compute the mean phase, a plurality of receive beams corresponding to each transmission of the transmit beam transmitted according to the transmit order are obtained. The receive beams are then grouped to an increment data group of a scan line index increasing direction and a decrement data group of a scan line index decreasing direction. The auto correlation is carried out for the increment and decrement data groups of the scan line increasing and decreasing directions, and weights are applied to respective auto correlation values for the increment and decrement data group. Thereafter, the auto correlation values with the weight applied are summed to compute the mean phase.

BRIEF DESCRIPTION OF DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
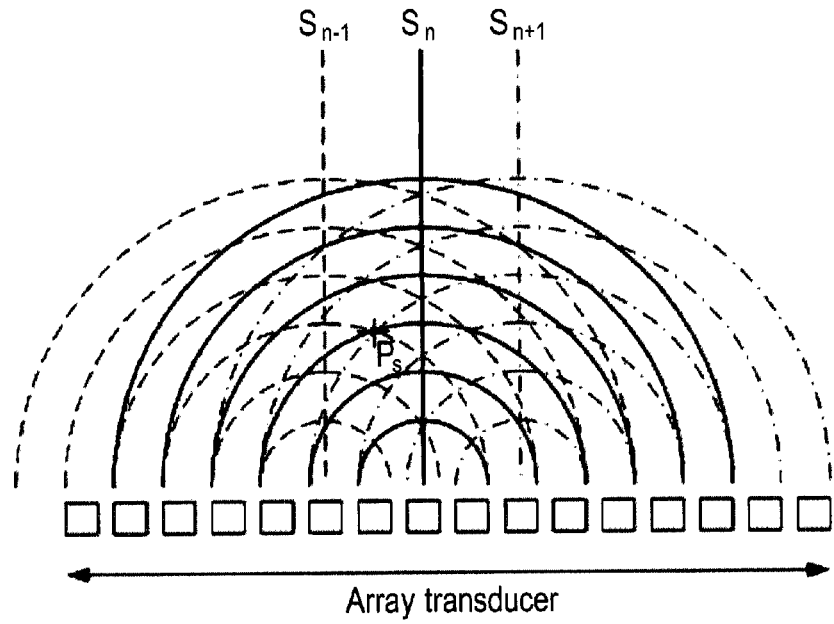
FIG. 1 is a schematic diagram showing a process of forming a general synthetic image.

When an image is obtained by using an array transducer in an ultrasound diagnostic system, the image may be obtained through one transmission of beam and one reception in response thereto. On the other hand, an ultrasound synthetic image is formed by making use of neighboring scan lines in addition to one scan line along which one transmit beam is transmitted, which have been already received. That is, the ultrasound synthetic image may be formed by using multi-receive beams in response to one time transmission of a transmit beam. For example, in order to obtain an $n^{th}$ scan line $S_n$, a transmission and a reception are typically carried out along the scan line $S_n$ to obtain an image. In case of an ultrasound synthetic image, however, the ultrasound synthetic image may be formed by combining neighboring scan lines $S_{n-m}, S_{n-(m-1)}, \ldots, S_n, \ldots, S_{n+(m-1)}, S_{n+m}$, wherein m>0, for the scan line $S_n$. In FIG. 1, $P_s$ represents a superimposed portion of wave fronts of waves transmitted along three scan lines, e.g., scan lines $S_{n-1}, S_n$ and $S_{n\_1}$. Thus, when a pixel corresponding to $P_s$ is obtained, the superimposed portion is considered to obtain an ultrasound image.

When a target object is a stationary object, an ultrasound synthetic image having a good resolution and a good signal to noise ratio (SNR) may be obtained. However, when the target object is a moving object (especially moving in an axial direction), an undesirable image may be displayed in an ultrasound synthetic image. That is, one scan line in the ultrasound synthetic image may be formed by using multi-receive beams obtained with a time delay or multi-receive beams responsive to one transmission beam such as bi-directional pixel based focusing (BiPBF). Thus, if a motion occurs in the target object and beam forming is carried out without considering the motion, then an incoherent sum may occur, which lowers the contrast resolution and SNR of the ultrasound synthetic image. Thus, the ultrasound synthetic imaging has not been used to form the TDI until now.

An image synthesizing process using BiPBF, which is one of transmit synthetic-aperture focusing methods capable of increasing a transmit power of the ultrasound signal by using signals from a plurality of transmit fields, may perform a transmit focusing and a receive focusing on all points. As illustrated by 2b of FIG. 2, a transmit focal point may be translated by referring to a virtual source element.

Figure 2:
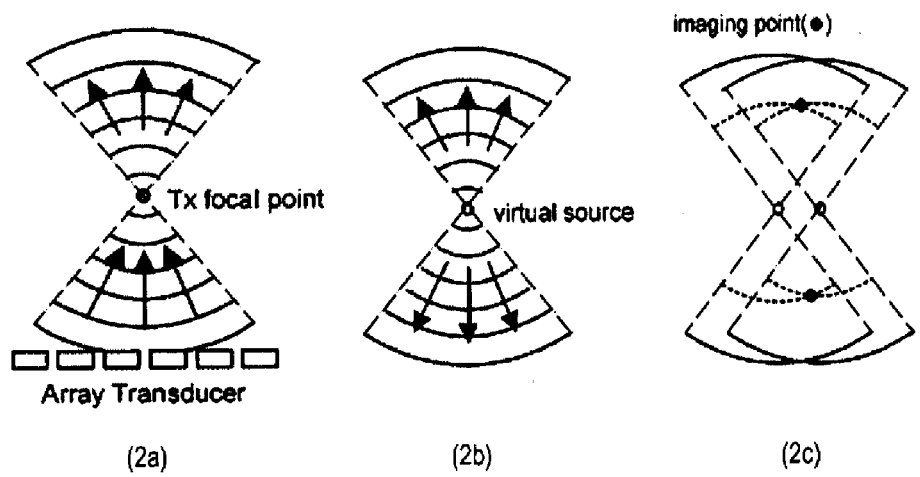
FIG. 2 is a schematic diagram showing examples of ultrasound radiation.

In FIG. 2, 2a shows a transmit field in a brightness (B) mode. As shown in 2a of FIG. 2, beams, which radiate from the array transducer, converges toward a focal point and then diverges in the shape of a circular wave within a limited angular extent. As shown by 2b of FIG. 2, a virtual source element, which is one of the array transducers, is located at a focal depth. The virtual source element may generate a circular wave back and forth with respect to itself. As shown by 2c of FIG. 2, transmit fields of two virtual source elements are superimposed at imaging points. One imaging point is shown before the focal depth and the other imaging point is shown after the focal depth with respect to a symmetric center of the circular field.

The image synthesizing process using BiPBF can maintain a uniform lateral resolution over all focal depths and reduce a side lobe level compared to other methods. Also, since the transmit power increases due to the synthesis of transmit fields, an ultrasound synthetic image having an enhanced SNR may be obtained through the image synthesizing process using BiPBF. However, the image synthesizing process using BiPBF may be restricted to imaging a stationary or slowly moving object. If the image synthesizing process using BiPBF is implemented to image a fast moving object, then the resolution may be degraded or the target object may disappear in the ultrasound synthetic image. Especially, a motion occurring in an axial direction may largely affect the ultrasound synthetic image compared to a motion occurring in a lateral direction. That is, while the ultrasound synthetic image based on BiPBF for the stationary target object has a relatively better image quality compared to an image based on the single transmission/reception method, the ultrasound synthetic image based on BiPBF for the moving target object may have a worse image quality than an image based on the single transmission/reception method.

Thus, if the ultrasound synthetic imaging process using BiPBF is implemented to produce TDI without any modification, then an image quality for the moving object may be deteriorated. As such, the present invention may produce the TDI by applying the ultrasound synthetic imaging process using BiPBF without repeatedly transmitting the ultrasound signal by the ensemble number to each scan line (a synthetic imaging processing is adopted rather than the single transmission/reception method). Especially, the present invention may remove an effect of the side lobe in the synthetic image, and estimate and compensate for a motion to thereby produce the TDI. Then, the TDI may be produced without lowering the frame rate while the ultrasound signal is not transmitted by the ensemble number to each scan line. Also, since the side lobe levels are removed, there is a merit that the TDI can be produced by using data corresponding to an ensemble number of different transmit scan lines.

One of the methods for simply and confidentially recognizing a motion in an axial direction at a B-mode image is a 2-dimensional tissue Doppler imaging (2D-TDI). The 2D-TDI may repeatedly transmit an ultrasound signal with an identical acoustic field at a constant time interval and detect a phase shift of echo signals to thereby find a mean Doppler frequency by using auto correlation or other methods.

The synthetic aperture imaging (SAI) may be similar to the 2D-TDI in terms of repeatedly transmitting an ultrasound signal. However, the SAI may transmit an ultrasound signal in a different acoustic field per transmission, which is different from the 2D-TDI. In the SAI, a wavefront of the acoustic field may be rotated in a constant angle per each transmission in view of each of the pixels. This rotation may cause the side lobes in a low resolution image, which is formed based on each transmission, to be also rotated. Thus, in case of a main lobe of an independent target object, a motion in an axial direction may be found to be similar to a tissue Doppler. However, a wrong motion may be detected at a position of side lobes of the target object even at adjacencies of the target object, which is not moved. As such, the present invention adopts a new transmission order of a transmit beam (e.g., non-sequential transmission of a transmit beam) for compensating for the wrongly detected motion and provides a phase detecting method through auto correlation to estimate and compensate for the motion, so that the side lobes may be removed. Accordingly, the TDI may be produced by using data of transmit scan lines in different locations as an ensemble.

Figure 3:
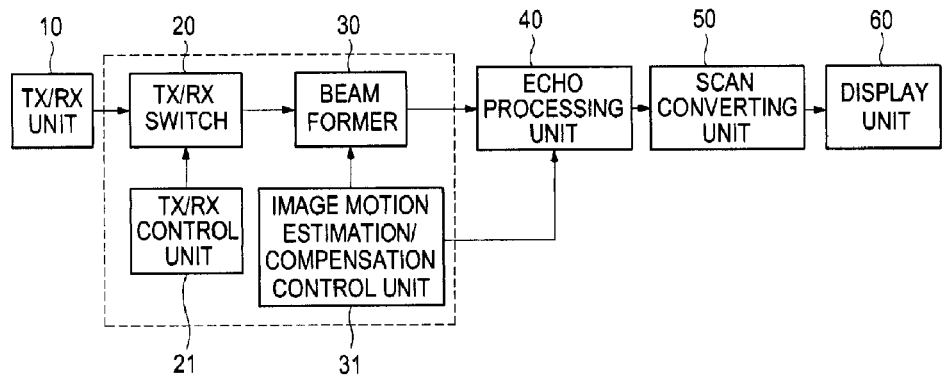
FIG. 3 is a schematic block diagram illustrating an ultrasound diagnostic system adopting a tissue Doppler image producing apparatus in accordance with one embodiment.
Figure 4:
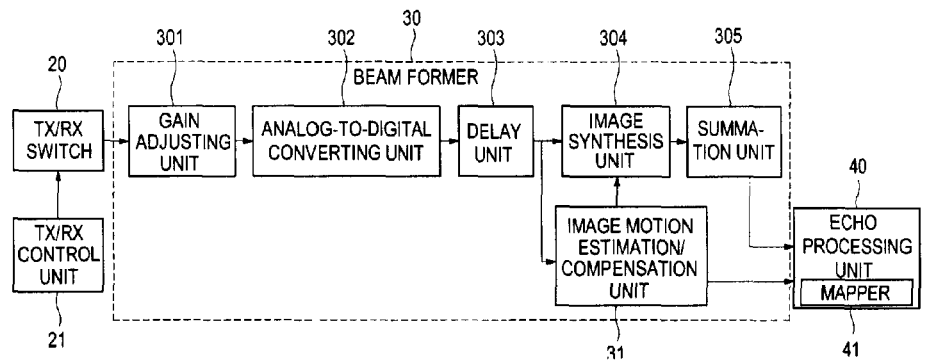
FIG. 4 is a schematic block diagram illustrating a beam former and an echo processing unit.
Figure 5:
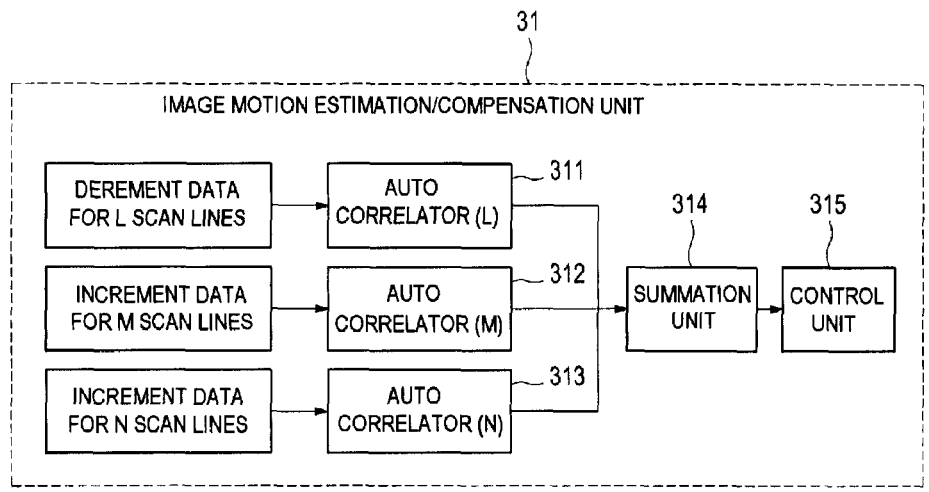
FIG. 5 is a schematic block diagram illustrating an image motion estimation/compensation control unit.

FIG. 3 is a schematic block diagram illustrating an ultrasound diagnostic system using a tissue Doppler image producing device of one embodiment. FIG. 4 is a block diagram illustrating a beam former 30 and an echo processing unit 41 of FIG. 3. FIG. 5 is a schematic block diagram illustrating an image motion estimation/compensation control unit 31 of FIG. 4.

A transmit/receive unit 10 may include a probe (not shown) containing an array transducer. The probe may be configured to transmit and receive ultrasound signals. The transmit/receive unit 10 may further include a transmitter (not shown) and an analog receiver (not shown). The array transducer may comprise a plurality of elements (e.g., 128 elements) and may be configured to output the ultrasound pulses in response to transmit pulses applied from the transmitter. The analog receiver may receive reflection signals (echo signals), which are the ultrasound pulses outputted from the respective elements of the array transducer reflected from the target object. The analog receiver may be configured to amplify the reflection signals, remove aliasing phenomenon and noises, and compensate for attenuation occurring while the ultrasound pulses are propagated into the target object.

A transmit/receive switch 20 may switch between a transmission and a reception of the ultrasound signals for the same elements. The transmit/receive switch 20 may be further configured to prevent a high power outputted from the transmitter from affecting the analog receiver. That is, when the transmission and reception are alternately carried out, the transmit/receive switch 20 may be configured to appropriately switch the transmitter and the analog receiver.

A beam former 30 may be configured to perform a receive focusing upon signals received at the respective transducer elements. The beam former 30 may include a gain adjusting unit 301, an analog-to-digital converting unit 302, a delay unit 303, an image synthesizing unit 304 and a summing unit 305. The gain adjusting unit 301 may be configured to compensate for gain of the analog receive signals received at the analog receiver. The analog-to-digital converting unit 302 may be configured to convert the analog receive signals to digital receive signals. The delay unit 303 may apply a different amount of delay, which depends on positions for receive focusing, to the digital receive signals (determined based on distance differences between the respective elements and a focal point). The image synthesizing unit 304 may be configured to synthesize the delayed signals to thereby form a receive-focused beam. The summing unit 305 may be configured to sum the receive-focused beams formed at respective channels.

An echo processing unit 40 may be configured to convert the radio frequency (RF) receive-focused beam into a baseband signal and perform an envelop detection with a quadrature demodulator, thereby obtaining an ultrasound image data corresponding to scan lines.

A scan converting unit 50 may store the receive-focused data from a predetermined point on the scan line and scan-convert the receive-focused data in a format capable of being displayed on a display unit 60. That is, the scan converting unit 50 may be configured to convert the ultrasound image data in an appropriate data format capable of being displayed.

The display unit 60 may display an image-processed ultrasound image.

Until now, the functions of elements for forming the ultrasound synthetic image in the ultrasound diagnostic system have been described.

The TDI producing apparatus in one embodiment may provide a specified sequence of the ultrasound transmit beam (i.e., transmission in a non-sequential transmit order) and generate data necessary for motion estimation and compensation (e.g., phase and power data formed in a pixel unit or a sample unit) by inputting data grouping receive beams in response to the ultrasound transmit beam into auto correlators 311-313. The TDI producing apparatus may compute data required for producing the TDI, i.e., velocities, powers and variances. In one embodiment, a transmit/receive control unit 21 may control the transmit/receive switch 20 such that the transmit beam is non-sequentially transmitted (see FIG. 6). The transmit/receive control unit 21 may group data of a scan line index ascending order and data of a scan line index descending order to an increment group data and a decrement group data, respectively, for the receive beams received in response to the transmission of the transmit beam in the non-sequential manner. The transmit/receive control unit 21 may control M and N numbers of increment group data of the scan line index ascending order and L numbers of decrement group data of the scan line index descending order to be inputted to auto correlators (311-313 in FIG. 5), respectively. The auto correlators 311-313 of the image motion estimation/compensation control unit 31 may extract phase and power data for the motion of the target object by using the increment group data of the scan line index ascending order and the decrement group data of the scan line index descending order. A summation unit 314 may sum the phase and power data of the increment and decrement groups and transfer the summed data to the control unit 315. The control unit 315 may generate pixel or sample-based mean phase and power data for the increment/decrement group data. The pixel or sample-based mean phase and power data are transferred to the echo processing unit. These pixel or sample-based mean phase and power data are data for producing TDI. Thus, the echo processing unit 40 may output a velocity, a power and a variance for the mean phase and power data through a mapper 41. The mapper 41 of the echo processing unit 40 may store velocities, powers and variances for the mean phase and power data. This is so that the mapper 41 may automatically output one of the velocities, one of the powers or one of the variances in response to the input of the mean phase and power data. Further, the mapper 41 may automatically output at least two velocities, powers or variances corresponding to the mean phase and power data. The mapper 41 may further perform post-processing functions, i.e., functions for an enhanced color display (e.g., flash rejection, etc.). A scan converting unit 50 may convert the ultrasound scan line signals transferred from the mapper 41 into monitor scan line signals so that the TDI may be displayed on a display unit 60. In such a case, the TDI displayed on the display unit 60 is a color image having high resolution for the moving target object like the stationary object. The TDI may be displayed as 2D-TDI or 3D-TDI. The TDI may be displayed together with the B-mode image formed through the ultrasound synthetic process.

The non-sequential manner transmission of a transmit beam set a plurality of scan lines (e.g., 9 scan lines) for the ultrasound synthetic image, defines sequential indices of the scan lines (e.g., index 0, index 1, index 2, ..., index 9), set an order of the transmit beam for the scan lines in a non-sequential manner in which increment and decrement of the indices are repeated (e.g., index 1, index 0, index 3, index 2, index 5, index 4, ...) and transmits the transmit beam according to the set transmission order. The ultrasound beam is transmitted in a non-sequential manner and a plurality of receive beams received in response to each transmission of the transmit beam are grouped into an increment data group of a scan line index ascending order and a decrement data group of a scan line index descending order. Auto correlation is performed on the increment and decrement data groups, weights are applied to respective auto correlation values for the increment and decrement data groups respectively, and then the auto correlation values with the applied weight are summed. This enables the effect of the side lobe to be removed. The summation value may become zero for the stationary object. However, the summation value may not be zero for the moving object. This value may be the mean phase and power of the moving object.

In FIG. 4, although it is illustrated that the image motion estimation/compensation control unit 31 exists in the beam former 30, the image motion estimation/compensation control unit 31 may exist in an exterior separated from the beam former 30. The position of the image motion estimation/compensation control unit 31 may not be limited thereto.

First, a phase of a main lobe and a side lobe in an ultrasound synthetic image for a stationary object and an ultrasound synthetic image for a moving object will be checked through the low resolution images (LRI). Then, the phase will be re-checked after setting a new transmission order of the transmit beams for the scan lines.

Figure 7:
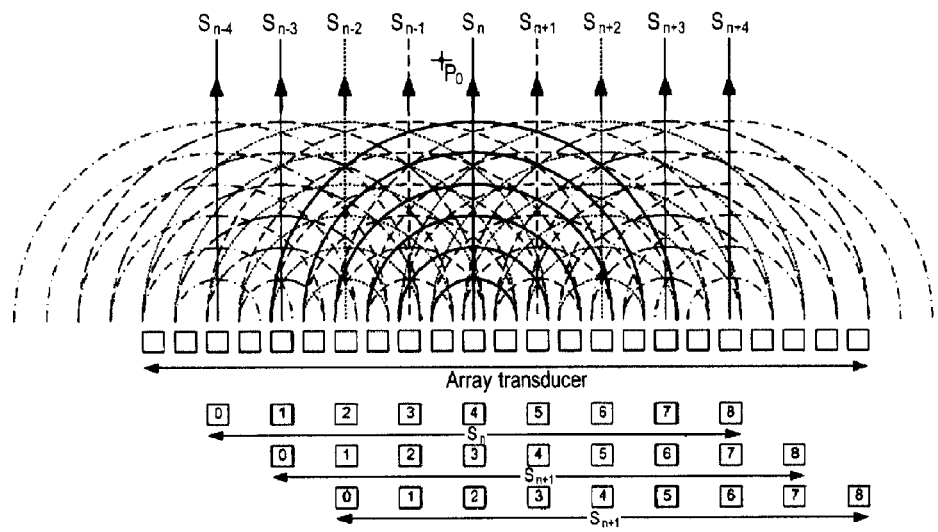
FIG. 7 is a schematic diagram showing an example of a synthetic aperture imaging method by using bi-directional pixel based focusing (BiPBF).
Figure 8:
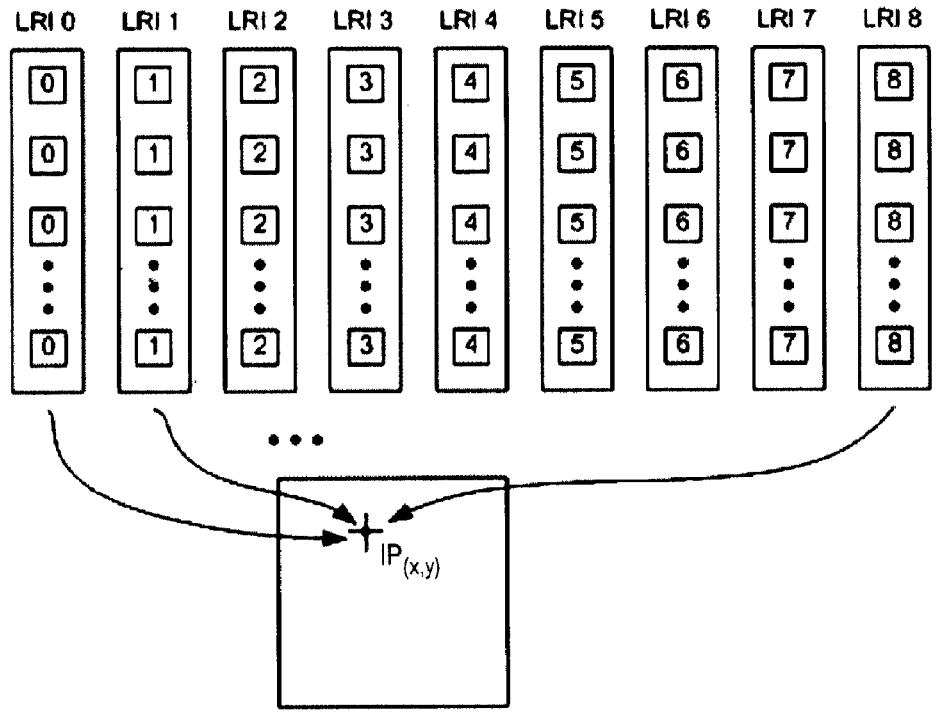
FIG. 8 is a schematic diagram showing a relation between low resolution images and scan lines.

FIG. 7 is a schematic diagram showing an example of a synthetic aperture imaging method by using the BiPBF. As illustrated in FIG. 7, a plurality of scan lines (N=9) participate in forming one synthetic scan line. Whenever the scan line for transmission is moved and increased, the participated scan lines are also moved. The numbers 0-8 represent an index order for auto correlation and N (=9) is the number of scan lines participating in image synthesis. N may be an ensemble number necessary for computing the mean phase and powers by using auto correlation function. It may be assumed that 0-8 wavefronts (data order inputted to auto correlation function, i.e., ensemble index) may be overlapped at an arbitrary point $P_0$ for image synthesis.

The number of LRI is 9 (N=9). Thus, the scan line may be increased by 0-8. Synthetic images may be configured by gathering respective index 0, index 1 ..., index 8. In such a case, an LRI corresponding to the index 4 is a typical image obtained by one transmission and one reception. When N=9, a phase shift of an arbitrary pixel point $P_0$ may be calculated from 9 LRIs.

In the ultrasound synthetic image obtained by using the BiPBF for a stationary object, an image for a main lobe may be indicated in the shape of a black hole as an auto correlation result since the phases for the main lobe are not changed. However, a phase may be changed due to the side lobe in spite of the stationary object. The phase shift becomes lower with closing to the main lobe. Thus, the phase shift due to the side lobe should be minimized regardless of the stationary or movement of the target object. If the motion is computed by auto correlation without considering the side lobes, then it may be determined that the stationary object moves in addition to the moving object. Hereinafter, an auto correlation procedure for the receive beams obtained through the transmission in the non-sequential manner to the stationary object or a moving object will be described in detail.

If the phase and power are computed through the auto correlation for the beams received in response to the transmit beam transmitted in a sequential manner, then the moving velocity should be 0 m/s in case of the stationary target object. However, a velocity component may be detected due to the effect of the side lobe. That is, if the transmit beam is transmitted in a sequential order for the stationary object, then a phase for the main lobe is not changed. However, a phase for the side lobe is rotated in a constant pattern in an x-y space. In such a case, the motion compensation may not be correct. Further, an accurate phase for the moving object should be estimated for the compensation. Thus, the present invention may transmit the transmit beam in a non-sequential manner (not in a sequential manner) to minimize the effect of the side lobes and then perform the auto correlation on the receive beams obtained in response to the transmission.

Figure 6:
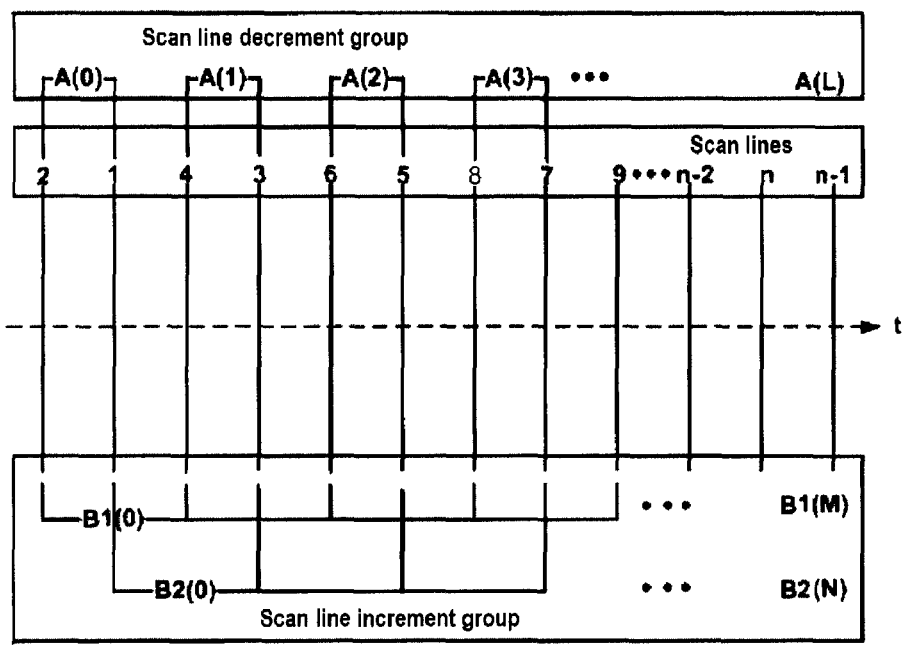
FIG. 6 is an exemplary diagram showing a transmission order of a transmit beam.

FIG. 6 is a schematic diagram showing an example of the transmit beam transmitted in a non-sequential manner. The scan lines may be divided into an increment group of a scan line index ascending order and a decrement group of a scan line index descending order, wherein the increment is +2 and the decrement is −1, which are different from each other. For example, the transmission is carried out not in an order of neighboring scan lines such as 1, 2, 3, 4 ..., but rather in an order of 2, 1, 4, 3, 6, 5 ... (non-sequential transmission) such that the increment and decrement of the scan line index, which are −1 and +2, are repeated. In such a case, assuming that a phase difference between a receive beam obtained in response to the first transmission and a receive beam obtained in response to the second transmission is indicated as a(1, 3), a mean phase difference calculated from a(2, 4), a(3, 5), a(8, 10), etc. (i.e., B group having a number difference of +2) for pixels located in the side lobe of the stationary target object may be denoted as B. Also, a mean phase difference calculated from a(2, 1), a(4, 3), a(6, 5), etc (i.e., A group having a number difference of −1) may be denoted as A. If the mean phase differences for the stationary target object are denoted as A and B, then the following equation (1) may be approximately obtained.

$$B = -2A \qquad \text{[Equation 1]}$$

$$A + \frac{1}{2} \times B = 0 \qquad \text{[Equation 2]}$$

As shown in equation (2), after A and B are individually calculated at each pixel, if weights are applied to A and B (e.g., weight "1" for the A group, weight "½" for the B group) and results are summed, then the wrong motion detection due to the rotation of the side lobe may be cancelled. Also, in case of the moving target object, even if a transmission order for the transmit scan lines is changed, the rotation of the phase due to the movement of the target object for each transmission may be defined as the following equation (3). Thus, if weights are applied and the applied results are summed, then a mean phase may be computed. This is so that a mean velocity of the target object may be accurately calculated such as the general 2D-TDI.

$$B = 2A \quad \text{[Equation 3]}$$

As such, the unnecessary phase difference due to the rotation of the side lobe may be reduced and only a phase difference due to a movement of the main lobe may be observed. The mean phase may be calculated by using the auto correlation. The auto correlation may be carried out as follows. Function $z_1(t)$ may be defined by functions $z(t)$ and $z^*(t-T)$ as the following equation (4)

$$z_1(t) = z(t) \times z^*(t-T) \quad \text{[Equation 4]}$$

$$z^*(t-T) = x(t-T) - jy(t-T) \quad \text{[Equation 5]}$$

wherein $z^*(t-T)$ is a conjugate complex delayed by a delay time T from the function $z(t)$ as shown in equation (5). If the function $z_1(t)$ is integrated over a specific time, then a result of the auto correlation function may be obtained as the following equation (6).

$$R(T, t) = \int_{t-nT}^{t} z_1(t') dt' = R_x(T, t) + jR_y(T, t) \quad \text{[Equation 6]}$$

wherein n, which is referred to as an ensemble number in an ultrasound image, represents the number of the consecutive transmit pulses in a constant direction.

The following equation (7) represents an auto correlation function for the receive beams corresponding to the increment group having the increment of +2. The following equations (8) and (9) represent the power and phase of the increment group of the scan line index ascending order. This process is carried out by an auto correlator 312 for the increment group of the scan line index increasing direction among the auto correlators 311-313 of the image motion estimation/compensation control unit 31.

$$R_I(T_I, t) = \int_{t-n_I T_I}^{t} z_{1I}(t') dt' = R_{xI}(T_I, t) + jR_{yI}(T_I, t) \quad \text{[Equation 7]}$$

$$|R_I(T_I, t)| = \sqrt{R_{xI}^2(T_I, t) + jR_{yI}^2(T_I, t)} \quad \text{[Equation 8]}$$

$$\Phi(T_I, t) = \tan^{-1} \frac{R_{yI}(T_I, t)}{R_{xI}(T_I, t)} \quad \text{[Equation 9]}$$

If a phase is calculated by applying a weight to the equation (9), then the following equation (10) may be obtained.

$$\Phi_S(T_I, t) = \frac{1}{2} \times \tan^{-1} \frac{R_{yI}(T_I, t)}{R_{xI}(T_I, t)} \quad \text{[Equation 10]}$$

The final results for the scan line index increasing direction may be expressed as the following equations (11) and (12).

$$R_{Sx1}(T_1, t) = |R_1(T_1, t)| \times \cos(\Phi_s(T_1, t)) \quad \text{[Equation 11]}$$

$$R_{Sy1}(T_1, t) = |R_1(T_1, t)| \times \sin(\Phi_s(T_1, t)) \quad \text{[Equation 11]}$$

The final results for the decrement group having the decrement of −1 may be expressed as the following equations (13) to (15). Equation (13) may represent auto correlation function for the part of decreasing the transmit scan line arrangement by −1. Equations (14) and (15) may represent a power and a phase of the decrement group of the scan line index descending order. This process may be carried out for the decrement group of the scan line index descending order by the autocorrelator 311 among the auto correlators 311-313 of the image motion estimation/compensation control unit 31.

$$R_D(T_D, t) = \int_{t-n_D T_D}^{t} z_{1D}(t') dt' = R_{xD}(T_D, t) + jR_{yD}(T_D, t) \quad \text{[Equation 13]}$$

$$|R_D(T_D, t)| = \sqrt{R_{xD}^2(T_D, t) + jR_{yD}(T_D, t)} \quad \text{[Equation 14]}$$

$$\Phi(T_D, t) = \tan^{-1} \frac{R_{yD}(T_D, t)}{R_{xD}(T_D, t)} \quad \text{[Equation 15]}$$

Eventually, the summation unit 314 may sum the results of autocorrelation performed for the respective increment group data of the scan line ascending order and decrement group data of the scan line descending order at the auto correlators 311-313 of the image motion estimation/compensation control unit 31. An output complex value of the summation unit 314 may be expressed as the following equations (16) and (17). The power of the corresponding pixel or sample may be defined as the following equation (18) and the phase may be defined as the following equation (19).

$$R_{Tx}(T, t) = R_{Sx1}(T_1, t) + R_{xD}(T_D, t) \quad \text{[Equation 16]}$$

$$R_{Ty}(T, t) = R_{Sy1}(T_1, t) + R_{yD}(T_D, t) \quad \text{[Equation 17]}$$

$$|R_T(T, t)| = \sqrt{R_{Tx}^2(T, t) + jR_{Ty}^2(T, t)} \quad \text{[Equation 18]}$$

$$\Phi_T(T, t) = \tan^{-1} \frac{R_{Ty}(T, t)}{R_{Tx}(T, t)} \quad \text{[Equation 19]}$$

Equation (18) may represent a pixel based mean power. Further, equation (19) represents a pixel based mean phase. By using this, a specific area based mean power and mean phase can be obtained. As such, the result of equations (16) and (17) may be expressed in space coordinates as the following equation (20).

$$R_{Tx}(T,t) \rightarrow R_{Px}(s,z), R_{Ty}(T,t) \rightarrow R_{Py}(s,z) \quad \text{[Equation 20]}$$

The equation (20) may be expressed as the following equations (21) and (22) so that it can be extended to a type having a specific area based mean phase.

$$R_{Rx}(i, j) = \frac{1}{k} \sum_{s=l}^{m} \sum_{z=n}^{0} R_{Px}(s, z) \quad \text{[Equation 21]}$$

$$R_{Ry}(i, j) = \frac{1}{k} \sum_{s=l}^{m} \sum_{z=n}^{0} R_{Py}(s, z) \quad \text{[Equation 22]}$$

The power may be computed together with the phase as the above equations to increase a degree of freedom of the compensation based on the power in the motion estimation and compensation. For example, when the power threshold is a reference, a much lower power may be ignored.

If TDI is produced by using the mean power and phase estimated by the suggested method, then TDI may be produced without time delay while the ultrasound signals are not repeatedly transmitted by the ensemble number for each scan line. The TDI may be produced by using data of transmit scan lines in different locations as an ensemble due to the removal of the side lobe level.

The transmit beam is transmitted in a non-sequential manner to the stationary object or the moving object, as shown in FIG. 6. Thus, if the auto correlation is performed upon the receive beams in response to the transmission, then an effect of the side lobe affecting the main lobe may be considerably reduced. Also, the effect of the side lobe may be reduced by adjusting the power threshold voltage.

Although the present invention has been described with reference to the embodiments and the accompanying drawings, the present invention is not limited to these embodiments. It should be understood by a person of ordinary skill in the art that various modifications, additions and substitutions can be made without departing from the scope and spirit of the invention. Thus, it should be noted that, in all aspects, the aforementioned embodiments are given by way of illustration and do not limit the present invention, as defined only the accompanying claims.

According to the present invention, a TDI may be produced without lowering a frame rate compared to the conventional method, while the ultrasound signals are not repeatedly transmitted by the ensemble number to each scan line. Also, since the side lobe levels are removed, there is a merit in that the TDI can be produced by using data corresponding to different transmit scan lines as an ensemble.

The invention claimed is:

1. A tissue Doppler image (TDI) producing device, comprising:
   a transmission/reception controller configured to:
   set a plurality of scan lines,
   define sequential indices of the scan lines,
   set a transmission order of a transmit beam for the scan lines in a non-sequential manner in which a decrement of −1 of a scan line index and an increment of +3 of the scan line index are alternated between neighboring scan lines arranged according to the transmission order,
   control a transmit beam to be transmitted to a target object according to the transmission order, and
   group a plurality of receive beams received in response to each transmission of the transmit beam into an increment data group in which an increment of the scan line index is +2 and a decrement data group in which a decrement of the scan line index is −1;
   an image motion estimation/compensation controller configured to:
   perform an auto correlation on the increment data group and the decrement data group, respectively, to obtain auto correlation values, and
   apply weights computed based on a mean phase difference of the increment data group and a mean phase difference of the decrement data group to respective ones of the auto correlation values for the increment data group and the decrement data group, and sum the auto correlation values with the weight applied thereto to compute a mean phase; and
   an image producer configured to output at least one of velocities, powers and variances in response to the mean phase to produce a TDI.

2. The TDI producing apparatus of claim 1, wherein the transmission/reception controller is further configured to obtain the plurality of receive beams corresponding to each transmission of the transmit beam transmitted according to the transmission order.

3. The TDI producing apparatus of claim 2, further comprising a display unit for displaying the produced TDI.

4. The TDI producing apparatus of claim 3, wherein image motion estimation/compensation controller is further configured to:
   perform the auto correlation upon respective ones of the increment data group and the decrement data group,
   apply the weights computed based on the increment of the scan line index in the increment data group and the decrement of the scan line index in the decrement data group to auto correlation values for the respective ones of the increment data group and the decrement data group; and
   sum the auto correlation values with the weights being applied thereto to compute a mean power.

5. The TDI producing apparatus of claim 4, wherein the auto correlation is performed based on a pixel unit or a predetermined area.

6. The TDI producing apparatus of claim 4, wherein:
   the image producer includes a mapper for storing velocities, powers and variances corresponding to respective ones of the mean phase and the mean power, and
   the mapper is configured to output one of the velocities, one of the powers or one of the variances, or output at least two values from the velocities, powers and variances, in response to an input of the mean phase and the mean power from the image motion estimation/compensation controller.

7. The TDI producing apparatus of claim 3, wherein:
   the TDI is one of a 2-dimensional TDI and a 3-dimensional TDI, and
   the TDI is displayed together with a B-mode image.

8. A method of producing a tissue Doppler image (TDI), comprising:
   setting, by a transmission/reception controller, a plurality of scan lines along which a transmit beam is transmitted;
   defining sequential scan line indices of the scan lines, the scan line indices of the scan lines increasing in a scanning direction;
   setting a transmission order of the transmit beam for the scan lines in a non-sequential manner in which a decrement of −1 of a scan line index and an increment of +3 of the scan line index are alternated between neighboring scan lines arranged according to the transmission order;
   transmitting, by a probe, the transmit beam according to the transmission order;
   obtaining a plurality of receive beams corresponding to each transmission of the transmit beam transmitted according to the transmission order by probe and grouping the receive beams into an increment data group in which an increment of the scan line index is +2 and a decrement data group in which a decrement of the scan line index is −1;
   performing, by an image motion estimation/compensation controller, an auto correlation upon the receive beams for respective ones of the increment data group and the decrement data group to obtain auto correlation values, to compute phases of the receive beams for the respective groups;
   applying weights computed based on a mean phase difference of the increment data group and a mean phase difference of the decrement data group to respective ones of the auto correlation values for the increment data group and the decrement data group, and summing the auto correlation values with the weight applied thereto to compute a mean phase; and outputting, by an image producer, at least one of velocities, powers and variances in response to the mean phase to produce a TDI.

9. The method of claim 8, further comprising displaying the produced TDI.

10. The method of claim 8, further comprising:
performing the auto correlation upon the receive beams for the respective ones of the increment and decrement data groups to compute powers of the receive beams for the respective groups;
applying weights computed based on the increment of the scan line index in the increment data group and the decrement of the scan line index in the decrement data group to the respective auto correlation values for the increment data group and the decrement data group;
summing the auto correlation values with the weight applied thereto to compute a mean power; and
outputting at least one of velocities, powers and variances in response to the mean phase and the mean power to produce a TDI.

11. The method of one of claim 10, wherein the auto correlation is carried out based on each pixel or a predetermined sample unit.

12. A method of producing a tissue Doppler image (TDI), comprising:
setting, by a transmission/reception controller, a plurality of scan lines along which a transmit beam is transmitted;
defining sequential scan line indices of the scan lines, the scan line indices of the scan lines increasing in a scanning direction;
setting a transmission order of the transmit beam for the scan lines in a non-sequential manner in which a decrement of −1 of a scan line index and an increment of +3 of the scan line index are alternated between neighboring scan lines arranged according to the transmission order;
transmitting, by a probe, the transmit beam according to the transmission order;
obtaining a plurality of receive beams corresponding to each transmission of the transmit beam transmitted according to the transmission order and grouping the receive beams into an increment data group in which an increment of the scan line index is +2 and a decrement data group in which a decrement of the scan line index is −1;
performing, by an image motion estimation/compensation control/unit, an auto correlation upon the receive beams for respective ones of the increment and decrement data groups to obtain auto correlation values, to compute powers of the receive beams for the respective groups;
applying weights computed based on a mean phase difference of the increment data group and a mean phase difference of the decrement data group to respective ones of the auto correlation values for the increment data group and the decrement data group, and summing the auto correlation values with the weight applied thereto to compute a mean power; and
outputting, by an image producer, at least one of velocities, powers and variances in response to the mean phase to produce a TDI.

13. The method of claim 12, further comprising displaying the produced TDI.

14. The method of claim 12, further comprising:
performing the auto correlation upon the receive beams for the respective ones of the increment and decrement data groups to compute phases of the receive beams for the respective groups;
applying weights computed based on the increment of the scan line index in the increment data group and the decrement of the scan line index in the decrement data group to the respective auto correlation values for the increment data group and the decrement data group;
summing the auto correlation values with the weight applied thereto to compute a mean phase; and
outputting at least one of velocities, powers and variances in response to the mean phase and the mean power to produce a TDI.

15. The method of claim 12, wherein the auto correlation is carried out based on each pixel or a predetermined sample unit.

* * * * *